(12) United States Patent
Marshall et al.

(10) Patent No.: US 6,945,982 B2
(45) Date of Patent: Sep. 20, 2005

(54) SKIN PRICKERS

(75) Inventors: Jeremy Marshall, Jericho (GB); Nick Hansen, Banbury (GB)

(73) Assignee: Owen Mumford Limited, Oxford (GB)

( * ) Notice: Subject to any disclaimer, the term of this patent is extended or adjusted under 35 U.S.C. 154(b) by 66 days.

(21) Appl. No.: 10/257,633

(22) PCT Filed: Feb. 15, 2002

(86) PCT No.: PCT/GB02/00682

§ 371 (c)(1),
(2), (4) Date: Mar. 20, 2003

(87) PCT Pub. No.: WO02/065910

PCT Pub. Date: Aug. 29, 2002

(65) Prior Publication Data

US 2003/0158568 A1 Aug. 21, 2003

(30) Foreign Application Priority Data

Feb. 17, 2001 (GB) .............................................. 0103977

(51) Int. Cl.[7] .............................................. A61B 17/32
(52) U.S. Cl. ...................................................... 606/182
(58) Field of Search ................................ 606/183, 182, 606/181; 604/209, 220

(56) References Cited

U.S. PATENT DOCUMENTS

| | | | |
|---|---|---|---|
| 5,100,427 A | * | 3/1992 | Crossman et al. .......... 606/182 |
| 5,487,748 A | | 1/1996 | Marshall et al. |
| 5,628,764 A | | 5/1997 | Schraga |
| 6,764,496 B2 | * | 7/2004 | Schraga ...................... 606/182 |

* cited by examiner

Primary Examiner—Anhtuan T. Nguyen
Assistant Examiner—Elizabeth Houston
(74) Attorney, Agent, or Firm—Young & Thompson

(57) ABSTRACT

A skin pricker has an elongate housing containing a spring-loaded lancet which, when released from a rearward, cocked position by a trigger, shoots forward momentarily to project the tip of its needle through one end of the housing. The lancet is then prevented by a spring ratchet from being returned again to the cocked position. The cocking can be done through a twist-and-pull cap initially covering the needle tip and extending through that one end of the housing, the user pushing the cap to retract the lancet from its initial position. To guard against the lancet being prematurely pulled forwards by the cap and being trapped against cocking by the ratchet, the lancet has a formation that will engage a part of the trigger.

15 Claims, 2 Drawing Sheets

SKIN PRICKERS

CROSS REFERENCE TO RELATED APPLICATION

This is the 35 USC 371 national stage of international application PCT/GB02/00682 filed on Feb. 15, 2002, which designated the United States of America.

FIELD OF THE INVENTION

This invention relates to skin prickers. It is concerned with skin prickers of the kind where a lancet is pushed back in its housing to a cocked position by its needle cap, which can then be removed by a twist and pull action, leaving the lancet ready to use. When fired, the needle tip momentarily projects and the bounce-back of the lancet withdraws it into the housing. Arrangements are made to prevent the lancet being pushed right back again, for example using the discarded cap, to the cocked position. So it is a single use device and has to be discarded.

BACKGROUND OF THE INVENTION

A convenient way of preventing such re-use is a spring ratchet mechanism. When assembled, the lancet is in an intermediate position with the ratchet ineffective against the rearward movement to the cocked position. But after firing, the lancet goes forward beyond its assembled position, and this allows a pawl to click past a tooth before the needle tip projects. The lancet is thus not prevented from bouncing back sufficiently to retract the needle tip, but it is arrested by the ratchet mechanism if any attempt is made to re-cock it.

There is a problem with this since a careless user can quite easily and accidentally pull the needle cap before the device is cocked. This can draw the lancet forward so that the ratchet mechanism engages. There is therefore an un-used pricker with the lancet trapped and unable to be cocked.

SUMMARY OF THE INVENTION

It is the aim of this invention to prevent that accidental mis-use.

According to the present invention there is provided a skin pricker comprising an elongate housing, a lancet within the housing, spring urged towards the forward end thereof momentarily to project its needle tip through an aperture at said forward end when the lancet is released from a cocked position, and a trigger carried by the housing with two modes of engagement with the lancet, in the first mode restraining the lancet from significant forward movement from its initial position but allowing retraction of the lancet to the cocked position, and in the second mode holding the lancet in said cocked position until operation of the trigger releases it.

Conveniently, the lancet has a ratchet type engagement with the trigger, snapping back past a tooth on the trigger as it reaches the cocked position. That tooth on the trigger can also be employed as the first mode restraint, co-operating with a projection on the lancet to stop the latter moving forwards. But when the trigger is operated to fire the lancet, its tooth will be lifted clear of the lancet, and will not obstruct that projection as it moves forward.

In the preferred form, a removable needle cap initially shrouds the needle tip and extends through the aperture. It can also serve as means by which the lancet can be pushed back from its initial position to the cocked position.

There will generally be means for ensuring that the lancet cannot be re-cocked after cocking and release, and this conveniently is a ratchet arrangement between the lancet and housing. In one form the lancet may have a spring finger pointing rearwardly and the housing will then have a tooth with which it co-operates. In the initial position of the lancet, the finger will lie against the tip of the tooth and as the lancet is pushed rearwardly, the finger will slide over that tip. When the lancet is fired, the rear end of the finger will go forward beyond the tooth before the needle tip projects and will be sprung to a position to abut the tooth as the lancet bounces back again retracting the needle tip. The lancet will thus be arrested and prevented from returning to the cocked position.

Preferably, there will be a symmetrical arrangement, with two fingers on opposite sides of the lancet co-operating with opposed teeth within the housing. This will ease assembly as the lancet can be placed in either one of two ways.

It would be possible to reverse the arrangement and have forwardly extending fingers on the housing and teeth on the lancet.

BRIEF DESCRIPTION OF THE DRAWINGS

For a better understanding of the invention, one embodiment will now be described, by way of example, with reference to the accompanying drawings, in which.

DETAILED DESCRIPTION OF THE INVENTION

Figure 1:
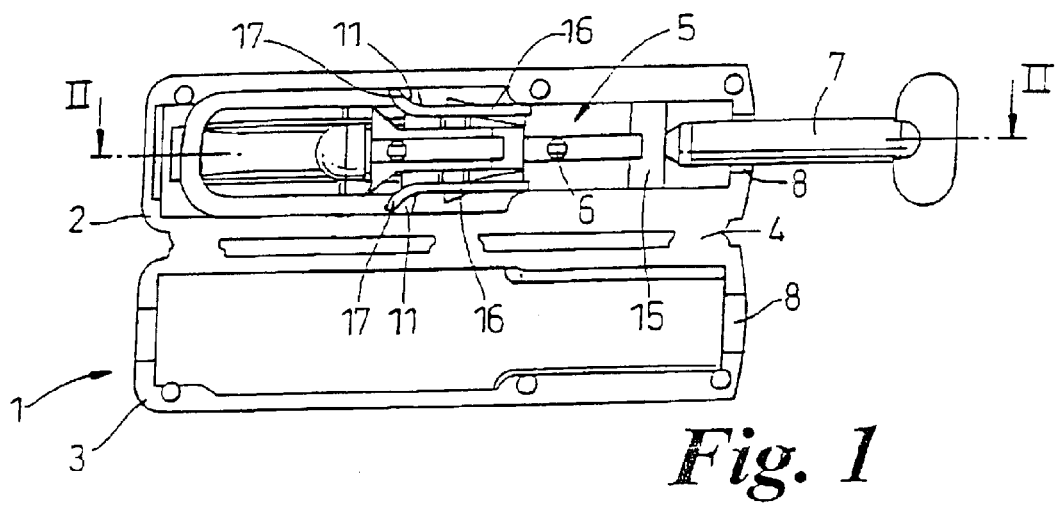
FIG. 1 is a plan view of a skin pricker in its assembled condition, but before closure of its housing.

The pricker has an elongate box-like housing 1 in two complementary halves 2 and 3 hinged together by an integral thin web 4 along one of the longitudinal sides. It houses a lancet 5 which has a moulded plastics body encasing needle 6 whose tip is initially shrouded by an elongate cap 7. There are cut-outs 8 at the forward ends of the halves 2 and 3 which combine to create an aperture through which the cap 7 can freely move, and through which the needle tip momentarily projects when the device is fired. The lancet is urged forwardly by a helical spring (not shown) acting between its rear end and the end of the housing 1 opposite the aperture 8. The firing of the lancet is by pressing the rear end of a trigger 9 integrally moulded with the half 2, this being of the rocker type and having a tooth 10 projecting into the housing at its forward end.

The half 2 also has two opposed teeth 11 on its side walls each with a shallow slope to the rear and a slight undercut on the forward side.

Figure 2:
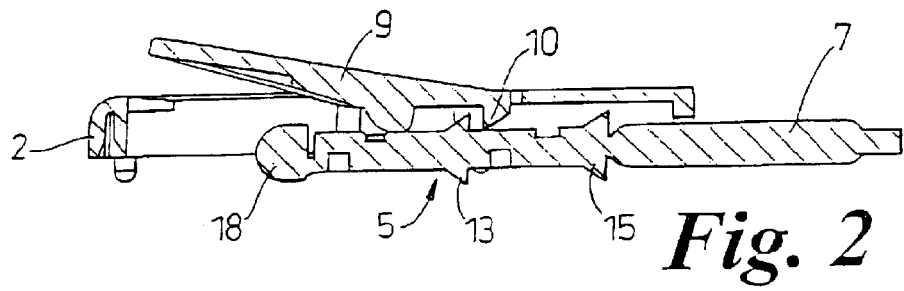
FIG. 2 is a section on the line II—II of FIG. 1.

The lancet 5 has a spine 12 encasing most of the needle 6. At about its mid-length it is expanded into an arrow-head-like formation 13 pointing rearwardly. Forward of this there are wings 14 making a rectangular plate-like structure, at whose transverse forward edge there is another formation 15 of arrowhead section pointing rearwardly. From the outer rear corners of the wings 14 there extend rearwardly fingers 16 which turn outwardly at their tips 17. At the rear end of the spine 12 there is a mushroom head 18 which locates the forward end of the helical spring. The lancet is generally symmetrical apart from minor features introduced for tooling reasons so that it does not matter which way up it is assembled into the housing, as shown in FIGS. 1 and 2. The tips 17 of the fingers 16 then lie just behind the teeth 11, and the tooth 10 of the trigger is just in front of the formation 13.

Supposing a user tries to remove the cap 7, with a twist and pull action he might shift the lancet 5 marginally forwards, but this movement will be arrested by the formation 13 engaging the tooth 10. The tips 17 will not override the teeth 11. Therefore, although the cap 7 may have come free, the pricker is not rendered useless and there is no problem in re-inserting the cap and pushing back the lancet. Normally, of course, the user will push back before attempting to remove the cap 7.

Figure 3:
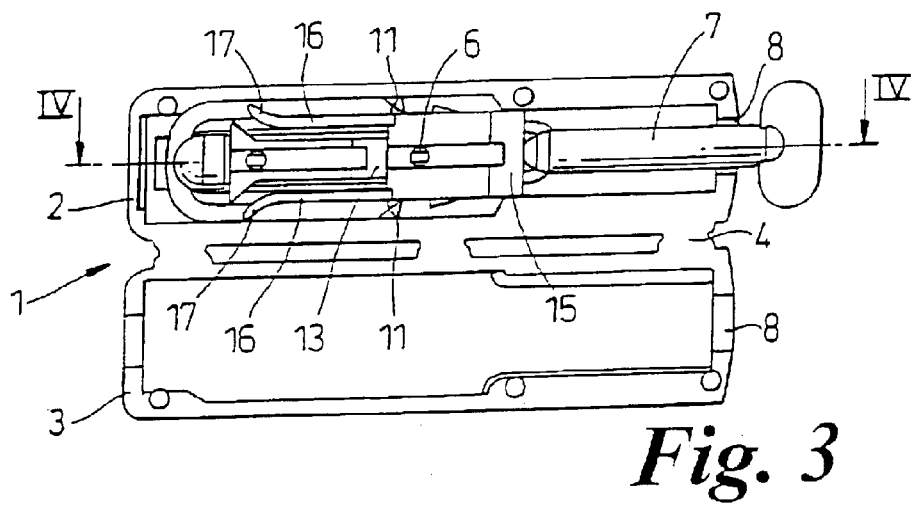
FIG. 3 is a plan view of the pricker in its cocked condition, the housing being shown open.
Figure 4:
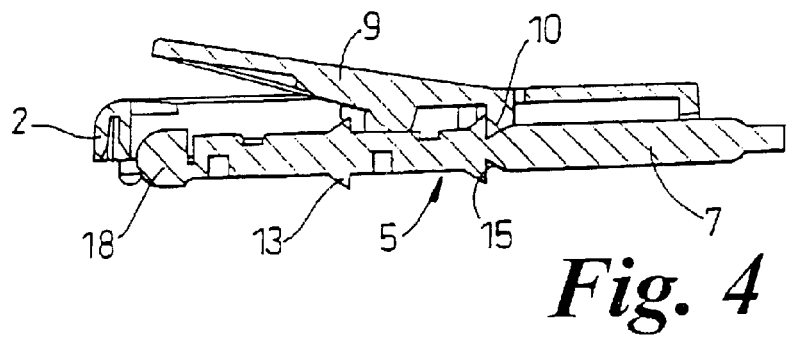
FIG. 4 is a section on the line IV—IV of FIG. 3.
Figure 5:
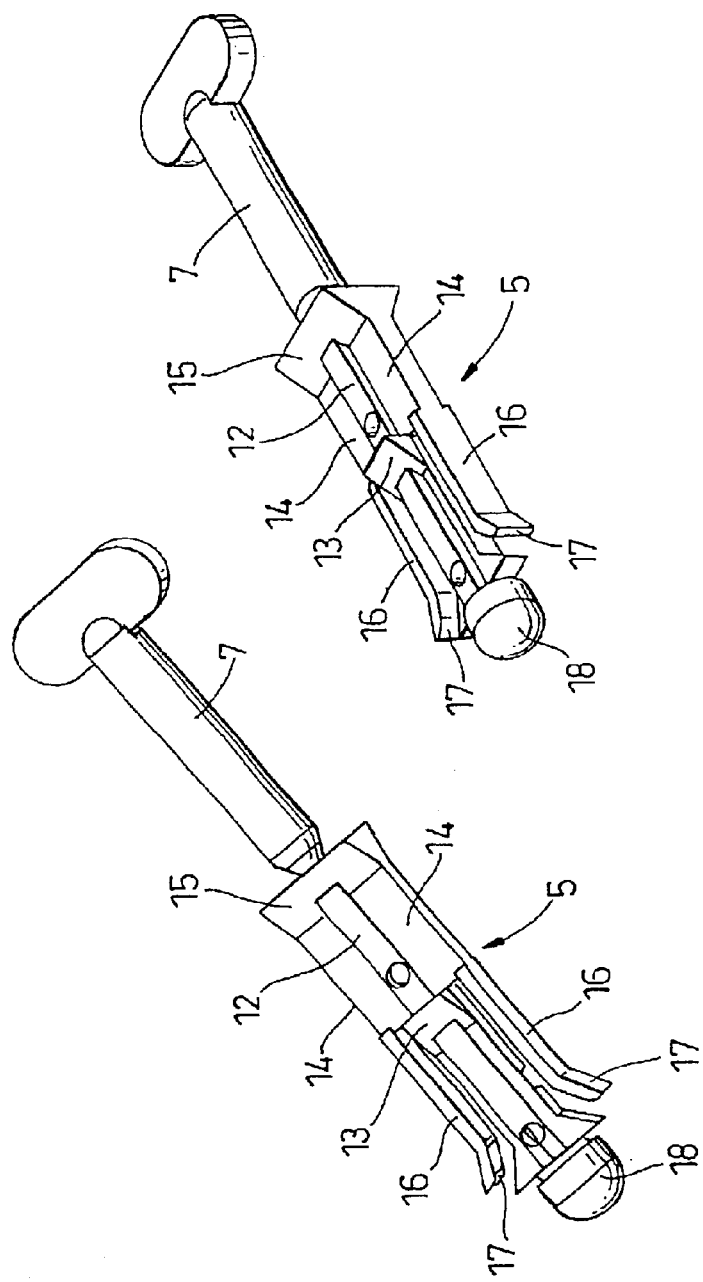
FIG. 5 shows three views of the lancet of the pricker.
Figure 5:
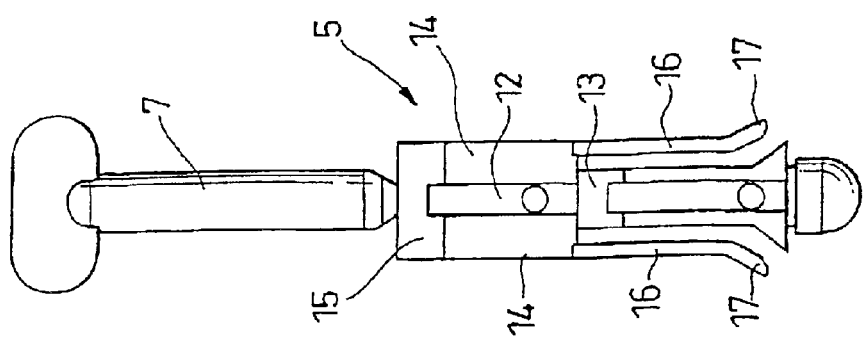

As the lancet 5 moves rearwardly, the fingers 16 simply slide over the tips of the teeth 11. But as the formation 15 reaches the tooth 10, the co-operating wedge-like surfaces tilt the trigger, which snaps over the formation 15 to hold the lancet in the rear, cocked position as shown in FIGS. 3 and 4. Then the cap 7 will be finally removed, the pricker applied to the skin and the trigger 9 pressed to release the lancet.

On firing, the lancet shoots forward beyond its assembled position of FIGS. 1 and 2, so that the fingers 16 flex inwardly as the tips 17 snap over the teeth 11. This happens just before the needle tip projects. The tooth 10 is held clear of the formation 13 and so does not impede the final part of the lancet's travel. After the tip projects, the lancet bounces back, but can go only a short distance, being arrested by the outwardly sprung tips 17 abutting by the teeth 11. Thus the pricker is non-re-usable.

What is claimed is:

1. A skin pricker comprising an elongate housing, a lancet within the housing, spring urged towards the forward end thereof, momentarily to project its needle tip through an aperture at said forward end when the lancet is released from a cocked position, and a trigger carried by the housing with two modes of engagement with the lancet, in the first mode restraining the lancet from significant forward movement from its initial position but allowing retraction of the lancet to the cocked position, and in the second mode holding the lancet in said cocked position until operation of the trigger releases it, the lancet having a ratchet type engagement with the trigger, snapping back past a tooth on the trigger as it reaches the cocked position.

2. A skin pricker as claimed in claim 1, wherein said tooth also serves as the first mode restraint, co-operating with a projection on the lancet to stop the lancet moving forwards but, when the trigger is operated to fire the lancet, being lifted clear of the lancet so as not to obstruct said projection as the lancet moves forward.

3. A skin pricker a claimed in claim 1, wherein a removable needle cap initially shrouds the needle tip and extends through the aperture, and also serves as means by which the lancet can be pushed back from its initial position to the cocked position.

4. A skin pricker as claimed in claim 1, and including means for ensuring that the lancet cannot be recocked after cocking and release.

5. A skin pricker as claimed in claim 4, wherein the means for ensuring that the lancet is no re-cocked is a ratchet arrangement between the lancet and housing.

6. A skin pricker as claimed in claim 5, wherein the lancet has a spring finger pointing rearwardly and the housing has a tooth with which it co-operates, the arrangement being such that, in the initial position of the lancet, the finger lies against the tip of the tooth and as the lancet is pushed rearwardly, the finger slides over that tip, and such that when the lancet is fired, the rear end of the finger goes forward beyond the tooth before the needle tip projects and is sprung to a position to abut the tooth as the lancet bounces back again retracting the needle tip.

7. A skin pricker as claimed in claim 6, wherein there is a symmetrical arrangement, with two fingers on opposite sides of the lancet co-operating with opposed teeth within the housing.

8. A skin pricker a claimed in claim 6, wherein the tooth and finger arrangement in reversed, there being at least one forwardly extending finger on the housing and an associated tooth on the lancet.

9. A skin pricker as claimed in claim 2, wherein a removable needle cap initially shrouds the needle tip and extends through the aperture, and also serves as means by which the lancet can be pushed back from its initial position to the cocked position.

10. A skin pricker as claimed in claim 2, and including means for ensuring that the lancet cannot be recocked after cocking and release.

11. A skin pricker as claimed in claim 3, and including means for ensuring that the lancet cannot be recocked after cocking and release.

12. A skin pricker as claimed in claim 10, wherein the means for ensuring that the lancet is not re-cocked is a ratchet arrangement between the lancet and housing.

13. A skin pricker as claimed in claim 11, wherein the means for ensuring that the lancet is not re-cocked is a ratchet arrangement between the lancet and housing.

14. A skin pricker as claimed in claim 12, wherein the lancet has a spring finger pointing rearwardly and the housing has a tooth with which it co-operates, the arrangement being such that, in the initial position of the lancet, the finger lies against the tip of the tooth and as the lancet is pushed rearwardly, the finger slides over that tip, and such that when the lancet is fired, the rear end of the finger goes forward beyond the tooth before the needle tip projects and is sprung to a position to abut the tooth as the lancet bounces back again retracting the needle tip.

15. A skin pricker as claimed in claim 7, wherein the tooth and finger arrangement is reversed, there being at least one forwardly extending finger on the housing and an associated tooth on the lancet.

* * * * *